United States Patent [19]

Pullman et al.

[11] Patent Number: 5,034,326
[45] Date of Patent: Jul. 23, 1991

[54] METHOD FOR REPRODUCING CONIFEROUS PLANTS BY SOMATIC EMBRYOGENESIS USING ADSORBENT MATERIALS IN THE DEVELOPMENT STAGE MEDIA

[75] Inventors: Gerald S. Pullman, Renton; Pramod K. Gupta, Federal Way, both of Wash.

[73] Assignee: Weyerhaeuser Company, Tacoma, Wash.

[21] Appl. No.: 426,331

[22] Filed: Oct. 23, 1989

[51] Int. Cl.$^5$ .................. C12N 5/04; A01H 7/00; A01H 5/00
[52] U.S. Cl. .................. 435/240.4; 435/240.45; 435/240.48; 435/240.49; 800/200; 800/DIG. 47; 800/DIG. 48
[58] Field of Search .......... 435/240.4, 240.45, 240.46, 435/240.47, 240.49, 240.54; 800/200

[56] References Cited

U.S. PATENT DOCUMENTS 4,217,730  8/1980  El-Nil ................................. 47/58

OTHER PUBLICATIONS

Attree, S. M., S. Budmir, and L. C. Fowke, 1990, Somatic embryogenesis and plantlet regeneration from cultured shoots and cotyledons of seedlings from stored seeds of black and white spruce (*Picea mariana* and *Picea glauca*). *Canadian Journal of Botany* 68: 30–34.

Becwar, M. R., T. L. Noland, and S. R. Wann, 1987, A method for quantification of the level of somatic embryogenesis among Norway spruce callus lines. *Plant Cell Reports*, 6: 35–38.

Becwar, M. R., S. R. Wann, and R. Nagmani, 1988, A survey of initiation frequency of embryogenic callus among ten families of *Pinus taeda* (loblolly pine). *Abstracts*, 4th International Conifer Tissue Culture Work Group, Aug. 8–12, 1988, Saskatoon, Saskatchewan, Canada.

Boulay, M. P., P. K. Gupta, P. Krogstrup, and D. J. Durzan, 1988, Development of somatic embryos from cell suspension cultures of Norway spruce (*Picea abies* Karst.). *Plant Cell Reports* 7: 134–137.

Bourgkard, F. and J. M. Favre, 1988, Somatic embryos from callus of *Sequoia sempervirens*, *Plant Cell Reports* 7: 445–448.

Buchheim, Julie A., Susan M. Colburn, and Jerome P. Ranch, 1989, Maturation of soybean somatic embryos and the transition to plantlet growth. *Plant Physiology* 89: 768–775.

(List continued on next page.)

*Primary Examiner*—Howard J. Locker
*Assistant Examiner*—Gary Benzion

[57] ABSTRACT

The invention is a method for reproducing coniferous trees by somatic embryogenesis using plant tissue culture techniques. It comprises a multistage culturing process. A suitable explant, typically the fertilized embryo excised from a mature or immature seed, is first cultured on a medium that induces multiple early stage proembryos. Preferably these proembryos are further multiplied in a second culture having reduced growth hormones. The early stage proembryos may then be placed in or on a late stage proembryo development culture which may have a significantly higher osmotic potential than the previous stage or stages to develop very robust late stage proembryos having at least about 100 cells and multiple suspensor cells. Culturing from this point continues in an embryo development medium very low in or lacking cytokinins and auxins but containing a relatively high concentration of exogenous abscisic acid and an adsorbent material, such as activated charcoal. The combination of abscisic acid and activated charcoal appears to increase the absolute number of embryos produced for most genotypes studied. Further, the vigor and morphology of the embryos is improved. After a period of several weeks cotyledonary embryos will have formed. These have a well defined bipolar structure with cotyledonary primordia at one end and a latent radicle at the other. If desired these embryos may be stored at about 4° C. for extended periods while still on the development medium.

15 Claims, 2 Drawing Sheets

OTHER PUBLICATIONS

Durzan, D. J. and P. K. Gupta, 1987, Somatic embryogenesis and polyembryogenesis in Douglas-fir cell suspension cultures. *Plant Science* 52: 229–235.

Gupta, Pramod K. and Don J. Durzan, 1985, Shoot multiplication from mature trees of Douglas-fir (*Pseudotsuga menziesii*) and sugar pine (*Pinus lambertiana*). *Plant Cell Reports* 4: 177–179.

1986a, Somatic polyembryogenesis from callus of mature sugar pine Embryos. *Bio/Technology* 4: 643–645.

1986b, Plantlet regeneration via somatic embryogenesis from subcultured callus of mature embryos of *Picea abies* (Norway spruce ). *In Vitro Cellular and Developmental Biology* 22: 685–688.

Gupta, Pramod and Don J. Durzan (cont.) 1987, Biotechnology of somatic polyembryogenesis and plantlet regeneration in loblolly pine, *Bio/Technology* 5: 147–151.

Hackman, Inger and Sara von Arnold, 1985, Plantlet regeneration through somatic embryogenesis in *Picea abies* (Norway spruce). *Journal of Plant Physiology* 121: 149–158.

1988, Somatic embryogenesis and plant regeneration from suspension cultures of *Picea glauca* (White spruce). *Physiologia Plantarum* 72: 579–587.

Hakman, Inger, L. C. Fowke, Sara von Arnold, and Tage Eriksson, 1985, The development of somatic embryos in tissue cultures initiated from immature embryos of *Picea abies* (Norway spruce), *Plant Science* 38: 33–35.

Johansson, Lars, 1983, Effects of activated charcoal in anther cultures, *Physiologia Plantarum* 59: 397–403.

Johansson, Lars, Barbro Andersson, and Tage Eriksson, 1982, Improvement of anther culture technique: activated charcoal bound in agar medium in combination with liquid medium and elevated $CO_2$ concentration. *Physiologia Plantarum* 54: 24–30.

Krogstrup, P., 1986, Embryolike structures from cotyledons and ripe embryos of Norway spruce (*Picea abies*). *Canadian Journal of Forestry Research*, 16: 664–668.

Lu, Chen-Yi and Trevor A. Thorpe, 1987, Somatic embryogenesis and plantlet regeneration in cultured immature embryos of *Picea glauca*. *Journal of Plant Physiology*, 128: 297–302.

Murashige, Toshio and Folke Skoog, 1962, A revised medium for rapid growth and bioassays with tobacco tissue cultures. *Physiologia Plantarum* 15: 473–493.

Nagmani, R. and J. M. Bonga, 1985, Embryogenesis in subcultured callus of *Larix decidua, Canadian Journal of Forest Research* 15: 1088–1091.

Nagmani, R. and M. R. Becwar, 1988, Factors affecting somatic embryo development in loblolly pine. *Abstracts*, 4th International Conifer Tissue Culture Work Group, Aug. 8–12, 1988, Saskatoon Saskatchewan, Canada.

Ranch, J. P., L. Oglesby, and A. C. Zielinski, 1985, Plant regeneration from embryo-derived tissue cultures of soybeans. *In Vitro Cellular & Developmental Biology*, 21: 653–658.

1986a, Plant regeneration from tissue cultures of soybean by somatic embryogenesis. In I. K. Vasil, ed. *Cell Culture and Somatic Cell Genetics*, vol. 3, pp. 97–110, Academic Press, New York.

1986b, Factors affecting the initiation and maintenance of embryogenic soybean tissue. Conference on Molecular and Cellular Biology of the Soybean, Iowa State University, Ames, Iowa.

Singh, Hardev, 1978, "Embryo" in *Embryology of Gymnosperms*, Chapter 11, Gebruder Borntrager, Berlin.

Teasdale, Robert D., Pamela A. Dawson, and H. W. Woolhouse, 1986, Mineral nutrient requirements of a loblolly pine. (*Pinus taeda* cell suspension culture. *Plant Physiology* 82:942–945.

Von Arnold, Sara and Inger Hakman, 1988, Regulation of somatic embryo development in *Picea abies* by abscisic acid (ABA). *Journal of Plant Physiology* 132: 164–169.

Ziv, Meira and Geula Gadasi, 1986, Enhanced embryogenesis and plant regeneration from cucumber (*Cucumis sativus* L.) callus by activated charcoal in solid/liquid double-layer cultures. *Plant Science* 47: 115–122.

Bu et al., (1988), Acta Phytophysiol sin 14(4) pp. 401–405 (Abstract relied on).

Whees, (1985), In/*Plant Cell Culture* a Practical Approach. Irh Press, Oxford, Washington DC., pp. 176–177.

Hakman et al., (1985), Plant Science 38, pp. 53–59.

Gupta et al., (1987), Biotechnology vol. 5, pp. 710–712.

Parrott et al., (1988), In Vitro Cellular & Developmental Biology, vol. 24, No. 8, pp. 817–820.

Fridborg et al., (1975), Physiol. Plant, vol. 34, pp. 306–308.

METHOD FOR REPRODUCING CONIFEROUS PLANTS BY SOMATIC EMBRYOGENESIS USING ADSORBENT MATERIALS IN THE DEVELOPMENT STAGE MEDIA

BACKGROUND OF THE INVENTION

The present invention is a method for reproducing coniferous plants by somatic embryogenesis using the techniques of plant tissue culture. It is especially suited for producing large clones of superior trees useful for reforestation.

Loblolly pine (*Pinus taeda*), its closely related southern pines, and Douglas-fir (*Pseudotsuga menziesii*) are probably the most important commercial species of temperate North American timber trees. Since the early 1940s, when serious private reforestation efforts began, literally billions of one and two year old nursery-grown trees have been planted on cut-over or burned forest lands. For many years these seedling trees were grown using naturally produced seed from cones collected as a part time effort of individuals seeking to supplement their incomes. As early as 1957 forest geneticists began to plant seed orchards using either seed or grafted scions obtained from superior trees. These trees were selected for such inheritable characteristics as rapid growth, straightness of bole, wood density, etc. Now in both the southern pine and Douglas-fir regions the bulk of the seed is produced from selected trees grown in seed orchards, some of them now second generation orchards.

Despite the fact that the orchards were stocked with superior trees, pollination often cannot be carefully controlled and frequently the seed trees are fertilized by wild pollen of unknown characteristics. For this reason, the characteristics of the progeny produced by sexual reproduction have not been as predictable as hoped and genetic gain could not be attained as rapidly as desired.

Beginning about 1960, techniques were developed for reproducing some species of plants by tissue culture. These were predominately angiosperms and usually ornamental house plants. The method employed use of a suitable explant or donor tissue from a desirable plant. This was placed on a series of culture media in which nutrients and growth hormones were carefully controlled from step to step. The usual progression was growth from the explant to a callus. The callus was placed on a budding medium where adventitious buds formed. These, in turn, were separated, elongated, and rooted to ultimately form plantlets. A plantlet has the nature of a seedling but is genetically identical to the explant donor plant.

Gymnosperms in general, and most forest tree species in particular, proved to be much more difficult to reproduce by tissue culture. It was not until about 1975 that Douglas-fir was successfully reproduced by organogenesis. Loblolly pine was successfully reproduced about two years later.

Culture by organogenesis is tedious and expensive due to the large amount of delicate manual handling necessary. It was soon recognized that embryogenesis was potentially a much more desirable method from the standpoints of quantity of plantlets produced, cost, and potential genetic gain. Work on embryogenesis of forest species began in the late 1970s. U.S. Pat. No. 4,217,730 to El-Nil describes one early process for embryogenesis of Douglas-fir. This approach was later set aside because advanced stage embryos and plantlets could not be readily obtained. However, other workers entered the field in increasing numbers and progress has been rapid even if it has not until the present time reached the commercial stage. A brief review of some of the most important work will follow. This is intended to be representative and is not fully inclusive of all the work in the field. Literature citations in the text are given in abbreviated form. Reference should be made to the bibliography at the end of the specification for full details of the literature cited.

The natural embryogeny of gymnosperms is described in great detail by Singh (1978). Conifer-type embryogeny is one of four types noted for gymnosperms. This includes virtually all of the important forest species except Sequoia.

Bourgkard and Favre (1988) describe what is the apparently successful production of plantlets by somatic embryogenesis of *Sequoia sempervirens*. As a historic note, this was one of the first forest tree species successfully reproduced by organogenesis.

Hakman and her coworkers have concentrated on Norway spruce (*Picea abies*), apparently with some success. In a paper by Hakman, Fowke, von Arnold, and Eriksson (1985) the authors describe the production of "embryos" but not plantlets. Hakman and von Arnold (1985) do suggest that they have successfully obtained plantlets. This latter paper is interesting for its comments on the variability within the species and the poor success with many of the seed sources used for explants. The authors suggest that this variability may be due to the physiological condition of the source material. However, other workers have noted great differences in behavior between recognized genotypes of the species.

Nagmani and Bonga (1985) describe embryogenesis from megagametophytes of *Larix decidua* by tissue culture. Some of the resulting embryos were stated to have further advanced to become plantlets of unknown ploidy established in soil.

Successful production of small quantities of plantlets has now been reported for loblolly pine. Teasdale, Dawson, and Woolhouse (1986) showed the criticality of proper mineral nutrients for cell suspension cultures of loblolly pine. The article by Becwar, Wann, and Nagmani (1988) is enlightening for the differences shown in performance between different families (or genotypes). Three families out of the ten tried accounted for most of their success. Even so, they appeared unable to grow cotyledonary embryos. A companion paper by Nagmani and Becwar (1988) showed development of *Pinus taeda* to the precotyledonary stage. In an earlier paper, Gupta and Durzan (1987) described their success in taking loblolly pine to the plantlet stage by embryogenesis. However, only one genotype was successfully taken to the plantlet stage and only one plantlet was produced. The authors note the need for "improved conversion rates" as well as other information before the process can be considered commercially practical.

Sugar pine (*Pinus lambertiana*) has also been cultured to the plantlet stage as reported by Gupta and Durzan (1986). The authors note a very low 1-2% conversion of embryos into plantlets.

The above researchers have also had success in producing Douglas-fir plantlets (Durzan and Gupta 1987). Again, the success ratio appears to be very low and with only a single genotype.

In an earlier application, U.S. Ser. No. 321,035, filed Mar. 9, 1989, now U.S. Pat. No. 4,957,866, the present inventors described an improved method for reproducing coniferous species by somatic embryogenesis. An intermediate high osmoticant culture medium was used to generate strong late stage proembryos, prior to the development of cotyledonary embryos in a medium containing abscisic acid. This application is herein incorporated by reference.

Activated charcoal has been widely used in tissue culture media where it is believed to function as an adsorbent for toxic metabolic products and undesirable amounts of residual hormones. Abscisic acid has also been recognized as being a useful plant hormone in cultures inducing conifer embryogenis; e.g., Boulay, Gupta, Krogstrup, and Durzan (1988). The combination of these two materials has been used by a number of workers, generally with indifferent or negative results. Johansson, Andersson, and Ericksson (1982) cultured anthers of several ornamental plant species using a two phase liquid over solid medium in which the agarified solid phase contained activated charcoal. The charcoal appeared to be useful for absorbing small amounts endogenous abscisic acid. In a related paper Johansson (1983) added exogenous abscisic acid in amounts varying by orders of magnitude from $10^{-9}$M to $10^{-3}$M to a charcoal containing medium. His conclusion was that abscisic acid completely inhibits embryogenesis at concentration above $10^{-4}$M. Further, he noted that the activated charcoal reduced the level of exogenous abscisic acid in the other cultures having lower concentrations thus allowing embryogenesis to proceed.

Ziv and Gadasi (1986) studied embryogenesis in several genotypes of cucumber (*Cucumis sativus L.*). They used liquid cultures as well as the two layer technique with activated charcoal in the solid layer of the medium and low (0.4 $\mu$M) levels of abscisic acid in the liquid layer. In the liquid cultures abscisic acid by itself only slightly improved embryo formation and was significantly more effective than the combination of abscisic acid with activated charcoal. Plantlet development in the liquid over solid cultures was slightly improved by the combination of the two materials.

Buchheim, Colburn, and Ranch (1989) suggest that exogenous abscisic acid and activated charcoal would probably not be a very useful combination of ingredients in a culture medium because of adsorption of the abscisic acid by the charcoal with subsequent loss of its biological effectiveness.

To the present inventor's knowledge, no one has heretofore shown the combination of abscisic acid and activated charcoal to be useful in the embryogenic tissue culture of coniferous species.

While the potential for achieving genetic gain using somatic embryogenesis is recognized as being very great, the problems to date have been so overwhelming that no commercial application has seemed close at hand for forest species. In fact, oil palm is the only tree reproduced by embryogenesis to have reached the stage of small plantation plantings. Until very recent times, possible commercial production of timber species by embryogenesis has remained no more than a fond hope in the minds of the people working in the field.

SUMMARY OF THE INVENTION

The present invention is a method of reproducing selected plants by somatic embryogenesis using tissue culture techniques. The method is particularly suitable for reproducing woody gymnosperms of the order Coniferales. It is especially well suited for generating large clones of superior forest trees for reforestation, including, species within the families Pinaceae, Cupressaceae, and Taxodiaceae. Most or all species within the genera Pinus, Picea, Tsuga, Pseudotsuga, Thuja, Juniperis, Larix, and Sequoia are believed to be well suited for multiplication by the present method.

The present method is particularly advantageous in that it enables greater quantities and more robust somatic embryos to be produced. This results in higher numbers of embryos that can be successfully converted into plantlets. Costs per plantlet can be significantly reduced over prior known culturing methods. In addition, use of the method generates embryos that can be retained for extended periods of time in cold storage without transferring them from a development medium.

A number of terms are known to have differing meanings when used in the literature. The following definitions are believed to be the ones most generally used in the field of botany and are consistent with the usage of the terms in the present specification.

"Auxins" are plant growth hormones that promote cell division and growth.

"Cytokinins" are plant growth hormones that affect the organization of dividing cells.

"Callus" is generally considered to be a growth of unorganized and either unconnected or loosely connected plant cells generally produced from culturing an explant.

"Embryogenic callus" is a callus-like mass that contains early stage proembryos attached to suspensors.

A "proembryo" is a cell or group of cells having the potential to become a plant but lacking defined meristematic organ primordia.

Figure 1:
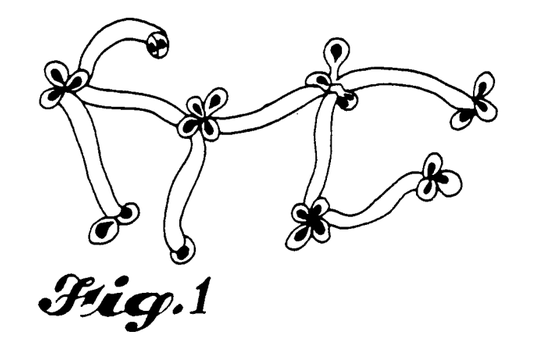
FIG. 1 shows early stage proembryos.

An "early stage proembryo" is a mass generally of 1-10 cells with dense cytoplasm and large nuclei that have the potential of forming a plant. The early stage proembryo is normally found as a head associated at the end of a long thin-walled suspensor cell (FIG. 1).

Figure 2:
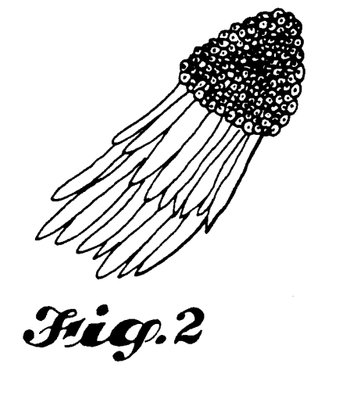
FIG. 2 shows late stage proembryos.

A "late stage proembryo" is a proembryo with a smooth embryonal head of at least about 100 cells associated with multiple suspensor cells. The late stage proembryo is a very robust advanced proembryo (FIG. 2).

Figure 3:
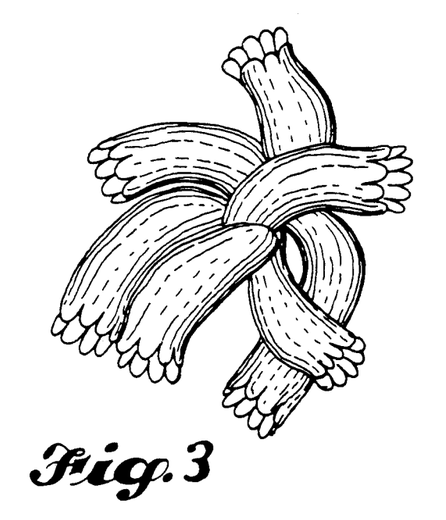
FIG. 3 depicts cotyledonary stage embryos.

A "cotyledonary embryo", sometimes simply referred to as an "embryo", has a well defined elongated bipolar structure with latent meristem with cotyledonary primordia at one end and a potential radicle at the opposite end. The cotyledonary structure frequently appears as a small "crown" at one end of the embryo (FIG. 3).

An "explant" is a piece of tissue taken from a donor plant for culturing.

A "meristem" or "meristematic center" is a group of tissue forming cells capable of further development into plant organs; e.g., shoots and roots.

An "osmoticant" is a chemical material used for controlling the osmotic potential of a solution. In the present context the solution would be a culture medium.

Figure 4:
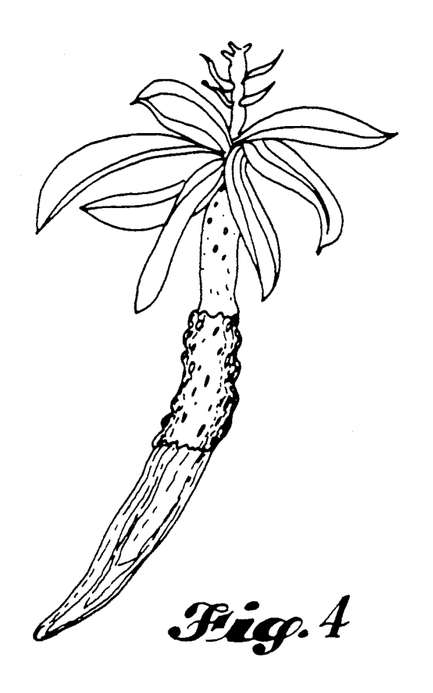
FIG. 4 shows a plantlet ready for transfer to soil.

A "plantlet" is a plant asexually reproduced by tissue culture (FIG. 4).

"Somatic embryogenesis" is the process using tissue culture techniques for generating multiple embryos from an explant. The embryos from a given tissue source will all be genetically identical.

The present method comprises a multistage culturing process. A suitable explant is first placed on an induction culture medium. This usually will contain relatively high quantities of growth hormones including at least one auxin and frequently one or more cytokinins. However, growth hormones at this initial stage are not always necessary or desirable for induction of early stage proembryos. A number of sources of explants may ultimately prove to be satisfactory for culturing. These include, but are not limited to, tissue from cotyledons, hypocotyls, epicotyls, buds, meristematic centers for buds or roots, and seed embryos. Seed embryos are presently preferred. In particular, for species which in the past have proved to be very difficult or impossible to propagate by somatic embryogenesis, the embryos from immature seeds may be preferred.

The first stage or induction medium will normally be one of those well known from past work which contain a balanced concentration of inorganic salts and organic nutrient materials, with plant growth hormones included as noted above. Auxins are normally present in concentrations which may be as high as about 250 μM/L, more typically not exceeding about 50 μM/L. Cytokinins, if present, are often in the neighborhood of about 40–50 μ/L, more typically not exceeding about 40 μM/L. The plant growth hormones may include at least one auxin and one cytokinin in a combined concentration not exceeding about 250 μM/L, more typically not exceeding about 100 μM/L. The particular auxins and cytokinins used and their exact concentrations, or whether they are used at all, will depend somewhat on the species being cultured and even on the particular genotype within that species. This is something that cannot be readily predicted but can be determined experimentally. Culturing during this stage may be carried out in the dark, under very low light conditions, or in full light until an embryogenic mass forms. Lighting conditions will depend in large part on the composition of the particular medium selected. This embryogenic mass has been described by various other names by researchers who have reported it in the past; e.g., embryogenic callus (Hakman and von Arnold 1985) or embryonal-suspensor mass (Durzan and Gupta 1987). It has the appearance of a whitish translucent mucilagenous mass containing early stage proembryos which are readily apparent by low power light microscopy.

Early stage proembryos from the first culture may be directly transferred to a late proembryo development culture medium having significantly reduced plant growth hormones and, for some species, a higher concentration of osmoticants. However, they are preferably first subcultured in a maintenance medium of similar osmotic potential to the induction medium for multiplication. This multiplication medium will also typically have the concentration of plant hormones significantly reduced below that of the induction medium. By "significantly reduced" is meant lowered by a factor which may typically be one whole order of magnitude.

The composition and use of the late proembryo development culture medium is frequently important to the success of the present process. It differs from the induction medium by having a similar reduced level of plant growth hormones to those present in the maintenance and multiplication medium. However, for certain species such as *Pinus taeda* and *Pseudotsuga menziesii* it differs from either of these earlier media in that the concentration of osmoticants should be significantly raised above that of the induction or multiplication media. The optimum osmoticant levels at each stage will usually differ for each species. The key factor is that proembryo quality or size may, if necessary, be improved by increased osmotic potentials. The embryo development step which follows requires reduction of this raised osmoticant level. However, some species such as *Picea abies* do not generally require this osmotic "spike" or it may only be necessary for some genotypes. In these cases late proembryo development may usually be achieved without a change in medium composition from the maintenance and multiplication medium.

Incubation is usually carried out in the dark or in greatly reduced light until robust late stage proembryos have formed. These may then be transferred to an embryo development medium which preferably lacks auxins and cytokinins entirely and has the level of osmoticants reduced, often back to that of the induction medium. A relatively high concentration of exogeneous abscisic acid is a necessary new component in this medium. This is used in combination with an adsorbent material, such as activated charcoal. The function of the adsorbent is not well understood. It is generally believed that it adsorbs phenolic and other toxic materials produced by natural metabolic processes. In the present case it may also operate to control concentration of abscisic acid and any other hormones present during the culturing period. After an appropriate length of time, again normally under dark or greatly reduced light photoconditions, cotyledonary embryos will form. These may then be transferred to a final medium for germination.

While the present inventors do not wish to be bound by any particular explanation, they believe that development of embryos to the cotyledonary stage is facilitated at this time by a relatively high initial concentration of abscisic acid which is gradually reduced to a lower level. This effect is achieved by the inclusion of an adsorbent such as activated charcoal in an appropriate amount. The adsorbent should be present in a sufficient amount and form to slowly adsorb the exogenous abscisic acid and metabolic waste products. It should not be present in such a high concentration as to deplete the abscisic acid in a very short time; e.g., in a matter of days. The combination of abscisic acid and adsorbent will usually require a higher initial concentration of abscisic acid than would be the case if no adsorbent was present in the medium.

The germination medium has no hormones, a lowered organic nitrogen content, and a further reduced level of osmoticants. After a sufficient time in darkness followed by light or a 16 hour light and 8 hour dark photoperiod the cotyledonary embryos will have developed into plantlets. These have a well developed radicle and cotyledonary structure and are ready for planting in soil.

An entirely unexpected advantage of the present process was the discovery that the more robust somatic embryos produced by the use of the abscisic acid-adsorbent combination could be readily stored for extended periods of time. Several genotypes of at least two coniferous species (*Pinus taeda* and *Picea abies*) have now been stored without loss of vitality for three months at 4°–5° C. without removing them from the development medium. This has not been possible with any degree of success before the present invention.

It is an object of the present invention to produce coniferous plantlets by somatic embryogenesis.

It is another object to produce a large clone of a genetically selected forest species for reforestation using the methods of somatic embryogenesis and plant tissue culture.

It is a further object to provide a method of somatic embryogenesis that will dependably and consistently provide coniferous plantlets in large quantities.

It is yet another object to provide a method of somatic embryogenesis that can dependably and consistently reproduce large clones of selected individuals of forest species that heretofore have not been successfully reproduced by this method.

It is still a further object to provide a method whereby superior genotypes of coniferous trees can be multiplied by tissue culture in the large quantities needed for reforestation.

It is also an object to provide a method that will produce somatic embryos in large quantities with improved robust morphology for conversion into plantlets.

It still another object to provide a method that generates robust somatic embryos capable of withstanding extended periods of cold storage.

These and many other objects will become readily apparent to those skilled in the art by reading the following detailed description, taken in conjunction with the drawings.

BRIEF DESCRIPTION OF THE DRAWINGS

The figures show various stages of plant embryogenesis in which.

DETAILED DESCRIPTION OF THE PREFERRED EMBODIMENTS

The process of the present invention is not limited to any single culture medium or to the use of specific growth hormones. Any of a number of well known media, such as that of Murashige and Skoog (1962), may be used. However, the present inventors have found the basal medium described in Table 1 to give excellent results, particularly when used for culturing loblolly pine (*Pinus taeda*). The basal medium is modified for each of the various culturing stages as shown in Table 2. Similar media particularly preferred for Norway spruce *Picea abies* are given in Tables 4 and 5.

TABLE 1

*Pinus Taeda* Basal Medium (Modified ½ P6 Basal Salts*)

| Constituent | Concentration, mg/L |
|---|---|
| $NH_4NO_3$ | 603.8 |
| $KNO_3$ | 909.9 |
| $KH_2PO_4$ | 136.1 |
| $Ca(NO_3)_2.4H_2O$ | 236.2 |
| $MgSO_4.7H_2O$ | 246.5 |
| $Mg(NO_3)_2.6H_2O$ | 256.5 |
| $MgCl_2.6H_2O$ | 50.0 |
| KI | 4.15 |
| $H_3BO_3$ | 15.5 |
| $MnSO_4.H_2O$ | 10.5 |
| $ZnSO_4.7H_2O$ | 14.4 |
| $NaMoO_4.2H_2O$ | 0.125 |
| $CuSO_4.5H_2O$ | 0.125 |
| $CoCl_2.6H_2O$ | 0.125 |
| $FeSO_4.7H_2O$ | 6.95 |
| $Na_2EDTA$ | 9.33 |
| Sucrose | 30,000. |
| myo-Inositol | 1,000. |

TABLE 1-continued

*Pinus Taeda* Basal Medium (Modified ½ P6 Basal Salts*)

| Constituent | Concentration, mg/L |
|---|---|
| Casamino acids | 500.0 |
| L-Glutamine | 1000.0 |
| Thiamine.HCl | 1.00 |
| Pyridoxine.HCl | 0.50 |
| Nicotinic acid | 0.50 |
| Glycine | 2.00 |
| Agar⁺ | 6,000. |
| pH adjusted to 5.7 | |

*According to Teasdale, Dawson, and Woolhouse (1986) as modified
⁺Used if a solid medium is desired

TABLE 2

Composition of Media for Different Stage Treatments $BM_1$—Induction Medium
    BM + 2,4-D (50 μM) + KIN (20 μM) + BAP (20 μM)
$BM_2$—Maintenance and Multiplication Medium
    BM + 2,4-D (5 μM) + KIN (2 μM) + BAP (2 μM)
$BM_3$—Late Proembryo Development Medium
    $BM_2$ + 9000 mg/L myo-inositol
$BM_4$—Embryo Development Medium
    BM + 4.0 to 8.0 mg/L abscisic acid
$BM_5$—Germination Medium
    BM modified by reducing sucrose to 20,000 mg/L,
    myo-inositol to 100.0 mg/L, glutamine to 200.0 mg/L,
    and casamino acids to 0.0 mg/L A number of abbreviations are used in the following text. These are in common use in the field of tissue culture.

BAP—$N^6$-benzylaminopurine (or $N^6$-benzyladenine), a cytokinin

KIN—kinetin (6-furfurylaminopurine), also a cytokinin 2,4-D—2,4-dichlorophenoxyacetic acid, an auxin NAA—2-Naphthylacetic acid (Naphthalene-2-acetic acid)

ABA—Abscisic acid

It will be understood by those skilled in the art that other plant growth hormones can be substituted for those just noted. As examples, IAA (indole-3-acetic acid), IBA (indole-3-butyric acid), and NAA (naphthalene-2-acetic acid) are effective auxins and 2-IP ($N^6$-isopentenylaminopurine) and zeatin are frequently used as cytokinins.

As a aid in comparing the present work with other published data, the following table of conversions from weight to molar concentrations might be useful.

| | 1 μM/L | 1 mg/L |
|---|---|---|
| BAP | 0.225 mg/L | 4.44 μM/L |
| KIN | 0.215 | 4.65 |
| 2,4-D | 0.221 | 4.52 |
| NAA | 0.816 | 5.38 |
| ABA | 0.264 | 3.78 |

In our earlier invention described in U.S. Ser. No. 321,035, we pointed out the importance of the control of osmotic potential of the media used in the various culturing stages. A large group of chemical materials are suitable as osmoticants. In general these are highly water soluble polyhydroxylated molecules that include either simple or complex sugars, hexitols, and cyclitols. The cyclitols are normally six carbon ring compounds that are hexahydroxylated. The most readily available cyclitol is myo-inositol but any of the other eight stereoisomeric forms, such as scyllo-inositol are believed to be quite suitable. Among the sugars, sucrose and glucose are known to be very effective but many others should prove to be equally useful. Sorbitol (D-glucitol), D-mannitol, and galactitol (dulcitol) are straight chain sugar alcohols suitable as osmoticants. Other materials suitable as osmoticants may include glycol ethers such as poly(ethylene glycol) and poly(propylene glycol).

EXAMPLE 1

The following schedule of treatments has been very successfully used for the growth of plantlets by somatic embryogenesis of loblolly pine (*pinus taeda*). Explants were immature embryos dissected from seeds 4 to 5 weeks after fertilization. Seeds were obtained from cones supplied by a Weyerhaeuser Company seed orchard located at Washington, N.C. The cones were stored at 4° C. until used. Immediately before removal of the immature embryos the seeds were sterilized using a modified method of Gupta and Durzan (1985). Briefly, this involves an initial washing and detergent treatment followed by a first sterilization in 30% $H_2O_2$ and a second in diluted 10% v/v household bleach. The additional $HgCl_2$ treatment used by Gupta and Durzan was not found to be necessary to ensure sterility. The explants were thoroughly washed with sterile distilled water after each treatment.

Stage I—Induction

Sterile dissected embryos were placed on a solid $BM_1$ culture medium and held in an environment at 22°–25° C. with a 24 hour dark photoperiod for a time of 3–5 weeks. The length of time depended on the particular genotype being cultured. At the end of this time a white mucilagenous mass had formed in association with the original explants. This appears to be identical with that described by Gupta and Durzan (1987). Microscopic examination revealed numerous early stage proembryos associated with the mass. These are generally characterized as having a long thin-walled suspensor associated with a small head generally having less than 10 individual cells, each with dense cytoplasm and large nuclei. Early proembryos are illustrated in FIG. 1.

Osmolality of the induction medium may in some instances be as high as 200 mM/kg. Normally it will be below 175 mM/kg and, more typically, about 160 mM/kg or even lower. The osmolality of the medium described above was 158 mM/kg.

Stage II—Maintenance and Multiplication

Early stage proembryos removed from the masses generated in the induction stage were placed on a $BM_2$ medium. This differs from the induction medium in that the growth hormones (both auxins and cytokinins) were reduced by a full order of magnitude. The temperature and photoperiod were again 22°–25° C. with 24 hours in the dark. Osmolality of this medium will typically be similar or identical to that of the induction medium. In the present example it was identical. Proembryos developed in this stage were similar in appearance to those from Stage 1 and were subcultured every 12–15 days on $BM_2$ medium.

Stage III—Late Stage Proembryo Development

Early stage proembryos from either Stage I or Stage II, preferably the latter, were placed on a $BM_3$ solid medium. This medium has the same growth hormone concentration as $BM_2$, however, the osmoticant was raised to a much higher concentration. In this case the osmoticant, myo-inositol, was at a concentration of 10,000 mg/L or 1% on a w/v basis. Osmotic potential was measured as 240 mM/kg. Temperature and photoperiod were the same as for Stages I and II. After 3 or 4 subcultures of about 12–15 days each, very robust late stage proembryos had formed. These are characterized by smooth embryonal heads generally having in the neighborhood of over 100 individual cells with multiple suspensors, as exemplified in FIG. 2. Osmotic potential of the late proembryo development medium should usually fall within the range of about 200–400 mM/kg for *Pinus taeda*. Most typically it should be in the neighborhood of about 1.5 times higher than that of the induction or multipliction media. As was noted earlier, the requirements for elevation of osmotic potential at this stage will vary for different species.

Alternatively, the Stage II and/or Stage III proembryos could be cultured for late proembryo development in suspension in a liquid medium of similar composition to $BM_3$ but lacking the agar. In this case subcultures could be made every 7–8 days.

It is preferred that early stage proembryos brought into Stage III culture should have a Stage II subculturing for rapid multiplication of the particular clone. However, on occasions where time may be of greater importance than quantity, early stage proembryos from Stage I may be taken directly into Stage III.

Stage IV—Embryo Development

The late stage proembryos from Stage III culture were transferred to a solid $BM_4$ medium. This medium either lacks growth hormones entirely or has them present only at very low levels and has the same lower level of osmoticants as Stages I and II. However, abscisic acid (5-(1-hydroxy-2,6,6-trimethyl-4-oxo-2-cyclohexen-1-yl)-3-methyl-2,4-pentadienoic acid) had been included here as a necessary material for further development. A critical aspect of the present invention is the further inclusion of an adsorbent material in this medium. The adsorbent may be chosen from a number of chemical materials having extremely high surface are and/or controlled pore size such as activated charcoal, soluble and insoluble forms of poly(vinyl pyrrolidone), activated alumina, silica gel, molecular sieves, etc. The adsorbent will normally be present in a concentration of about 0.1–5 g/L, more generally about 0.25–2.5 g/L. The contribution of the adsorbent appears to be complex and is not well understood. Adsorbent materials, especially activated charcoal, have been widely used in the past in various culture media. However, the particular combination of activated charcoal with relatively large amounts of abscisic acid in a late stage somatic embryo development medium is believed to be entirely new. The prevailing wisdom found in the literature clearly teaches away from use of this combination, especially at this point in the process.

The osmotic potential of this medium will generally be no greater than about 175 mM/kg. In the present case it was measured as 168 mM/kg. As before, development was carried out in complete darkness at a temperature of 22°–25° C. Development time was 4–6 weeks after which elongated cotyledonary embryos 4–5 mm long were present. These appeared as represented in FIG. 3.

Stage V—Germination

Cotyledonary embryos from Stage IV were placed on solid $BM_5$ medium for germination. This is a basal medium lacking growth hormones which has been modified by reducing sucrose, myo-inositol and organic nitrogen. After about 6–8 weeks under environmental conditions of 23°–25° C. and a 16 hour light/8 hour dark photoperiod the resulting plantlets were approximately 20 mm in length and had a well developed radicle and hypocotyl and green cotyledonary structure and epicotyl. The young plantlets are shown in FIG. 4.

Because of the reduced carbohydrate concentration, the osmotic potential of the germination medium is further reduced below that of the development medium. It will normally be below about 150 mM/kg and was, in the present example, about 100 mM/kg.

Stage VI—Plant growth

Plantlets from Stage V were removed from the culture medium and planted in a soil comprising equal parts of peat and fine perlite.

To the present time, three distinct genotypes of *Pinus taeda* have been successfully cultured through Stage V. Some of the plantlets have already been successfully transferred to soil and these are growing with good vigor. Two additional genotypes are being multiplied in Stage II prior to Stage III treatment. In work that preceeded that just described, all five genotypes when cultured without the Stage III high osmoticant treatment ultimately browned and died in Stage IV. Stated differently, the method failed completely when early stage *Pinus taeda* proembryos from Stage II were taken directly into Stage IV, as is taught in the prior art.

While inorganic salts and pure simple organic chemicals generally behave similarly in culture media regardless of supplier, there are occasions when this is not the case for the more complex materials. Without intending endorsement of any product over available alternatives, chemicals from the following suppliers were used throughout the experiments to be described in the examples. Agar was obtained from Difco Laboratories, Detroit Michigan. Where specified as "tissue culture agar" the supplier was Hazleton Biologics, Inc., Lenexa, Kans. Casamino acids, a casein hydrolysate, was also supplied by Difco Laboratories. Activated charcoal was obtained from Sigma Chemical Company, St. Louis Mo., as their grade NuC-4386.

EXAMPLE 2

The combination of ABA and activated charcoal in the Embryo Development Medium has proved to be very effective not only with *Pinus taeda* but with other important conifer species such as *Picea abies* and *Pseudotsuga menziesii*. In the following experiments the Loblolly Pine Basal Media of Tables 1 and 2 were used. In the Embryo Development Medium the ABA was adjusted as described in Table 3 and activated charcoal was included in a concentration of 2.0 g/L. All of the ingredients except the abscisic acid were combined, autoclaved, and cooled to 50°-60° C. A filter sterilized solution of ABA was then added and mixed. After 10 minutes the medium was poured into petri dishes.

Late stage proembryo cells of two genotypes, grown as described in the first example, were settled from a suspension culture, the supernatant liquid poured off, and 1-1.5 mL of the settled cells were plated on the solid Embryo Development Medium in 5 cm dishes. These cultures were incubated in the dark at about 22° C. for six weeks. Control cultures having 2 and 4 mg/L ABA without activated charcoal were also prepared. The following results were obtained.

TABLE 3

| Medium Composition | | Embryos Produced | |
|---|---|---|---|
| ABA, mg/L | Activated Charcoal g/L | Genotype A | Genotype B |
| 2.0 | 0.0 | 2.5 | — |

TABLE 3-continued

| Medium Composition | | Embryos Produced | |
|---|---|---|---|
| ABA, mg/L | Activated Charcoal g/L | Genotype A | Genotype B |
| 4.0 | 0.0 | 5.5 | — |
| 20.0 | 2.0 | 0 | 0 |
| 40.0 | 2.0 | 2 | 2 |
| 60.0 | 2.0 | 4 | 3 |
| 80.0 | 2.0 | 10 | 4.5 |
| 100.0 | 2.0 | 8.5 | 2 |

The embryos produced on the charcoal containing media were of better morphology with a well developed cotyledonary structure but without evidence of germinating precociously when compared to those grown without activated charcoal in the medium. The media described here are not represented as being optimized for the species or any genotype.

EXAMPLE 3

Some coniferous species are relatively easier to propagate by somatic embryogenesis than others. Coastal redwood, *Sequoia sempervirens*, is considered be be a relatively easy species while Norway spruce, *Picea abies*, is usually thought to be of only moderate difficulty. Most members of the genus Pinus as well as Douglas-fir, *Pseudotsuga menziesii*, are regarded as very difficult. This has posed a major challenge to researchers since the latter two genera include a major percentage of the worlds most economically important timber species. Even though past researchers have reported success with somatic embryogenesis of several pines and of Douglas-fir, others in the field have frequently not been able to duplicate the work of these competent investigators. There are probably several reasons for this. Most certainly, one of them is over optimism on the part of researchers who have achieved and reported early stage embryogenesis or embryo-like structures but who later have not been able to succeed in producing significant numbers of cotyledonary embryos or plantlets. Another is the great differences in performance between different genotypes within a given species. *Picea abies* is a case in point. As noted earlier it is usually regarded as a species of only moderate difficulty to reproduce by somatic embryogenesis using present state-of-the-art technology. However, there are some genotypes of *Picea abies* that haven proven intractable to all previous efforts. Most researchers have limited themselves to working with only one or two genotypes that are known from past experience to give good results.

Figure 5:
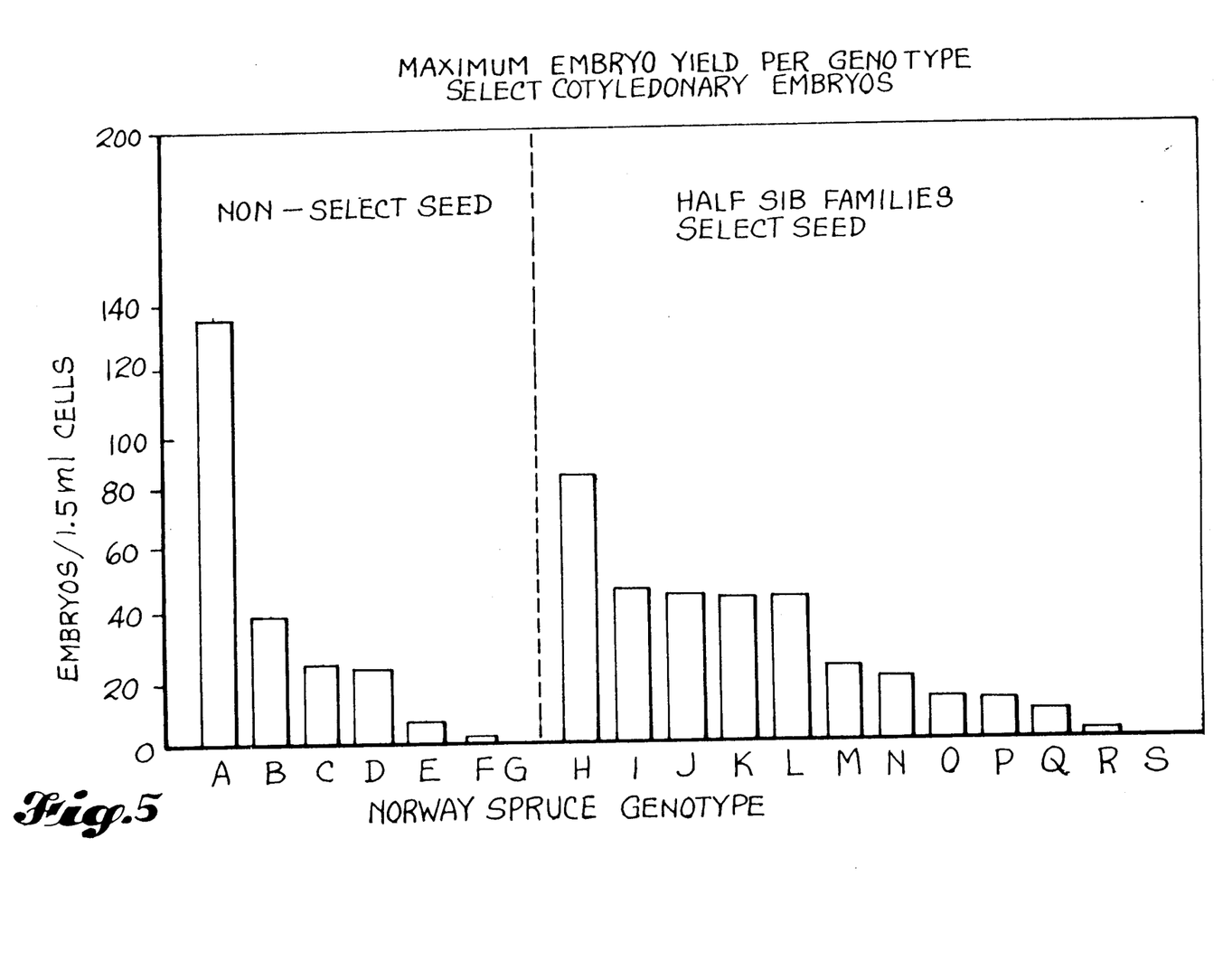
FIG. 5 shows the variation in behavior in tissue culture of various genotypes of a single coniferous species.

The present method has resulted in successful production of late stage proembryos and cotyledonary embryos on 23 of the 26 genotypes of *Picea abies* that have been investigated to date. This sample includes a considerable number of previously intractable genotypes. FIG. 5 shows the maximum yield of embryos per culture plate for 19 genotypes grown on the same nonoptimized culture (Medium No. 2 as described in Example 6). Seven of these are from non-select wild seed and twelve are select seed from known half-sib orchard families. The enormous differences in behavior constituting two full orders of magnitude, especially within the non-select seed, are immediately apparent. As has been noted earlier, similar results have been obtained with *Pinus taeda*, although not all genotypes have been processed to the later stages of treatment to the present time. Excellent results have also been obtained with *Pseudotsuga menziesii* where 17 of 22 genotypes have developed cotyledonary embryos. Culturing on many of these genotypes is still in progress and has not advanced to the germination stage. However, to date plantlets from 17 genotypes have been transferred to soil resulting in at least 200 established plants.

While the plant growth hormone usages noted in Table 2 are near optimum for loblolly pine, different concentrations and mixtures may prove more suitable for other species. It is fairly well established that growth hormones are usually necessary in Stages I-III, although some workers have apparently achieved early stage proembryos using growth hormone-free media. However, even when initially cultured on hormone-free media, these early stage proembryos were then transferred to cultures having the usual growth hormones. These hormones may in some instances be a single auxin or a mixture of auxins with or without one or more cytokinins. As a general rule the total concentration of all growth hormones should be below about 250 μM/L, preferably below about 100 μM/L in the Stage I medium. These concentrations should be reduced about tenfold in the Stage II and Stage III media.

TABLE 4

*Picea Abies* Basic Culture Media

| Constituent | Concentration, mg/L | |
|---|---|---|
| | A[(1)] | B[(2)] |
| BASAL SALTS | | |
| $NH_4NO_3$ | — | 206.3 |
| KCl | 372.5 | — |
| $KNO_3$ | 50.0 | 2340.0 |
| $KH_2PO_4$ | 85.0 | 85.0 |
| $MgSO_4.7H_2O$ | 160.0 | 185.0 |
| $CaCl_2.6H_2O$ | 220.0 | 220.0 |
| KI | 0.415 | 0.415 |
| $H_3BO_3$ | 3.10 | 3.10 |
| $MnSO_4.H_2O$ | 8.45 | 8.45 |
| $ZnSO_4.7H_2O$ | 4.30 | 4.30 |
| $NaMoO_4.2H_2O$ | 0.125 | 0.125 |
| $CuSO_4.5H_2O$ | 0.0125 | 0.0125 |
| $CoCl_2.6H_2O$ | 0.0125 | 0.0125 |
| $FeSO_4.7H_2O$ | 13.90 | 13.93 |
| $Na_2EDTA$ | 18.65 | 18.63 |
| ORGANIC ADDITIVES | | |
| Sucrose | 10,000. | 30,000. |
| myo-Inositol | 50.0 | 1000.0 |
| Casamino acids | 500.0 | 500.0 |
| L-Glutamine | 750.0 | 450.0 |
| Thiamine.HCl | 0.05 | 1.00 |
| Pyridoxine.HCl | 0.05 | 0.50 |
| Nicotinic acid | 0.25 | 0.50 |
| Glycine | — | 2.00 |
| L-Asparagine | 50.0 | — |
| pH | 5.8 | 5.7 |

[(1)]Institute of Paper Chemistry medium (Becwar, Noland, and Wann 1987)
[(2)]Gupta and Durzan medium $BM_3$ (1986b).

TABLE 5

Composition of *Picea Abies* Media for Different Stage Treatments $BM_I$—Induction Medium
  $BM_A$[(1)] + NAA[(3)] (10.8 μM) + BAP[(4)] (4.4 μM) + 7.0 g/L Difco agar.
$BM_M$—Maintainance and Multiplication Medium
  $BM_B$[(2)] + 2,4-D[(5)] (5 μM) + BAP (2 μM) + KIN[(6)] (2 μM). 6.0 g/L Difco agar added if solid medium is desired.
$BM_D$—Cotyledonary Embryo Development Medium
  $BM_B$ + 40.0 mg/L Arginine + 100 mg/L Asparagine + 6.0 g/L Tissue Culture Agar + Abscisic acid (as specified) + Adsorbent (e.g., activated charcoal) (as specified). $KNO_3$ is reduced to TABLE 5-continued Composition of *Picea Abies* Media for Different Stage Treatments 1170 mg/L in basal salts.
$BM_G$—Germination Medium
  $BM_B$ with $KNO_3$ reduced to 1170 mg/L, myo-Inositol reduced to 100 mg/L, Sucrose reduced to 20.0 g/L, and L-Glutamine and Casamino acids removed. 2.5 g/L of Adsorbent and 6.0 g/L of Tissue Culture Agar are added.

[(1)]Basic medium A from Table 4
[(2)]Basic medium B from Table 4
[(3)]2-Naphthylacetic acid (Naphthalene-2-acetic acid)
[(4)]$N^6$-Benzylaminopurine
[(5)]2,4-Dichlorophenoxyacetic acid
[(6)]Kinetin

EXAMPLE 4

The following screening experiment was made as a comparison between embryo development stage cultures containing only abscisic acid as a hormone additive with cultures containing a mixture of abscisic acid and activated charcoal. Mature *Picea abies* seed embryo explants were cultured on an Initiation Medium and Maintenance Medium as described in Tables 4 and 5. Explants were incubated in light of an intensity approximately 50 $\mu Em^{-2}sec^{-1}$. In this case the Induction Medium $BM_1$ had a relatively low carbohydrate content with a resulting low osmolarity of about 62 mM/kg. After an early stage embryogenic mass had developed, it was transferred to a solid and later to a liquid liquid Maintenance and Multiplication Medium $BM_M$ having a higher osmolarity of about 158 mM/kg. In this case the proembryos had attained a sufficiently late stage of development without the need for further culturing on a very high osmotic potential Late Proembryo Development Medium. These proembryos were settled and washed twice with liquid Embryo Development Medium $BM_D$ of Table 5 to which 10 mg/L of abscisic acid had been added. The washed cells were then drained on polyester pads. Approximately 2 mL of the washed cells were transferred to solid Embryo Development Medium $BM_D$ on 50 mm petri dishes. The growing cells were transferred twice at two week intervals to fresh media of the same composition. Culture room conditions were about 23°-24° C. in darkness throughout the experiment. The following table shows the compositions of the media used and the results obtained.

TABLE 6

| Medium Composition $BM_D$ | | Cotyledonary Embryos, |
|---|---|---|
| ABA, mg/L | Activated Charcoal, g/L | Average Yield/2 mL |
| 2.0 | 0 | 18.6 |
| 5.0 | 0 | 20.0 |
| 7.5 | 0 | 13.0 |
| 10.0 | 0 | 12.9 |
| 25.0 | 0 | 14.7 |
| 25.0 | 2.5 | 2.0 |
| 150.0 | 2.5 | 4.1 |
| 100.0 | 2.5 | 16.1 |
| 250.0 | 2.5 | 0.1 |

The ABA/charcoal media did not in general produce as many cotyledonary embryos in this experiment as the media with ABA alone. However, it was noted that the embryos produced on the media containing charcoal were frequently larger and of superior morphology to those cultured on the media containing only ABA. This experiment showed that embryos could be successfully cultured on media having relatively high concentrations of ABA and activated charcoal. Further, there was an indication that these embryos would have superior strength to those cultured on media containing only ABA.

It was noted during the experiment that development and mass growth on the charcoal containing media was so rapid that 10-14 days after starting the experiment most growth had stopped and the mass containing the embryos appeared dry. This suggested that available liquid was absorbed during early growth and may have become limiting.

The above experiment was carried out on three additional genotypes of *Picea abies*. In these tests no preliminary washes with ABA-containing medium were given. Results were variable. One genotype produced no cotyledonary embryos under any conditions. Another produced an average of 10.2 embryos on the media without charcoal and only 0.4 embryos on the charcoal containing media. The third genotype produced an average of only 1.7 embryos on the ABA only media and 2.0 embryos on the charcoal containing media.

It should be noted that the above reported experiments were of a preliminary screening nature only and do not represent optimized conditions. They were primarily made to see if the use of activated charcoal in the cotyledonary embryo development stage would be advantageous.

EXAMPLE 5

In a followup experiment to that just described, five genotypes of *Picea abies* were cultured as described above using a solid cotyledonary development medium containing 100 mg/L ABA and 2.5 g/L activated charcoal. This time the liquid $BM_M$ medium containing the proembryos was simply settled and the supernatant liquid poured off. Then 2 mL of the settled cells were pipetted onto the surface of the solid medium without washing or further draining in order to provide additional water for the system.

Embryos were visible within two weeks and harvestable by 3½ weeks. One genotype produced 34 robust cotyledonary embryos per mL of settled cells. Another produced 5.3 embryos per mL. The other genotypes produced few or no embryos.

160 cotyledonary embryos of the best performing genotype were transferred to a germination medium, incubated three weeks in the dark, transferred to fresh media and moved to the light. About 25% of these embryos began epictyl development after five weeks.

Again, it should be noted that no optimization of the ABA-charcoal ratio had been attempted.

EXAMPLE 6

Another set of experiments was made under conditions similar to the previous example in which activated charcoal in the cotyledonary embryo development medium was varied between 0 and 2.5 g/L and ABA varied between 5 and 100 mg/L. Four genotypes of *Picea abies* was used in the experiment. At least five replicates were made at each test condition.

Media compositions are given in the following table.

TABLE 7

| Medium No. | ABA, mg/L | Charcoal, g/L | Average Embryos/mL, Genotype | | | |
|---|---|---|---|---|---|---|
| | | | A | B | C | D |
| 1 | 100 | 2.5 | 46 | 0 | 0.5 | 13.2 |
| 2 | 50 | 1.25 | 102 | 0 | 1.8 | 9.5 |
| 3 | 10 | 0.25 | 76 | 0 | 0.6 | 20.4 |

TABLE 7-continued

| Medium No. | ABA, mg/L | Charcoal, g/L | Average Embryos/mL, Genotype | | | |
|---|---|---|---|---|---|---|
| | | | A | B | C | D |
| 4 | 10 | 0.10 | 18 | 0 | 0.2 | 5.4 |
| 5 | 5 | 0.0 | 0 | 0 | 0 | 0 |

Medium No. 2 containing 50 mg/L ABA and 1.25 g/L activated charcoal appeared to be significantly better than the others from the standpoints of number and vigor of embryos formed.

In a further modification of this experiment the best performing genotype above (Genotype A) was transferred onto the medium supported on laboratory filter paper. The experiment was replicated using the same culture media as above. As is seen in the following table, the results of cultures grown on agar medium alone and on filter paper supported on agar media are generally comparable. This opens up the possibility of direct mass transfer to germination or other media with a considerable savings in handling required. It further opens the possibility of a system in which either the charcoal or ABA is located on the filter paper with the other component being in the medium.

TABLE 8

| Medium No. | ABA, mg/L | Charcoal, g/L | Average Embryos/mL, | |
|---|---|---|---|---|
| | | | Directly on Agar | On Filter paper |
| 1 | 100 | 2.5 | 46 | 43 |
| 2 | 50 | 1.25 | 102 | 93 |
| 3 | 10 | 0.25 | 75 | 55 |
| 4 | 10 | 0.10 | 17 | 30 |
| 5 | 5 | 0.0 | 0 | 0 |

EXAMPLE 7

A comparison was made using four methods of culturing *Picea abies* at the embryo development stage. The first method used Embryo Development Media containing both ABA and activated charcoal. One subset was a replication of the Medium 2 composition from the previous example that gave the best results. Another subset used reduced amounts of both ABA and activated charcoal. In the second method the charcoal was omitted from the culture medium but the late stage proembryos were first coated with activated charcoal by rinsing them with a charcoal-containing liquid medium. The third method first cultured the late stage proembryos on a medium containing only activated charcoal followed by culturing on a medium containing only ABA. Finally, cultures were made on ABA-containing medium without any charcoal. In one subset of this method the growing embryos were transferred three times to fresh medium. In the other subset the embryos remained on the original medium the entire culturing period.

Two new genotypes of *Picea abies* not tested in the earlier examples were used for the present set of experiments. Results are given below. The compositions of all the media used are given in the Table 9. Late stage proembryos, cultured as in the last three examples, were used for all trials.

TABLE 9

| Medium No. | Composition |
|---|---|
| 1 | $BM_D$ (Table  ) — 15 mg/L ABA + 0.75 g/L activated charcoal |

TABLE 9-continued

| Medium No. | Composition |
| --- | --- |
| 2 | $BM_D$ + 50 mg/L ABA + 1.25 g/L activated charcoal |
| 3 | $BM_M$ without hormones or agar + 2.5 g/L activated charcoal |
| 4 | $BM_D$ + 10 mg/L ABA |
| 5 | $BM_D$ + 15 mg/L ABA |
| 6 | $BM_D$ + 10 g/L activated charcoal |
| 7 | $BM_D$ + 5 mg/L ABA |

PROCEDURES & RESULTS

First Method—ABA/Activated Charcoal Medium 1.0 mL of settled late stage proembryos was pipetted directly onto replicate 5 cm plates of media 1 and 2 above and cultured in the dark at about 22° C. for six weeks.

| Embryos Produced | Genotype A | Genotype B |
| --- | --- | --- |
| Medium 1 | 54.0 | 26.3 |
| Medium 2 | 83.0 | 92.5 |

These embryos had improved apical domes, hypocotyl region and root primordia when compared with embryos cultured on a development medium using ABA alone. Also a greater number of embryos were produced using the charcoal containing media. Ultimately the germination rate and successful growth into plantlets was also increased over a control group grown without activated charcoal.

Second Method—Activated Charcoal Coated Embryos on ABA Medium

Settled late stage proembryos were suspended in Medium 3 above, settled, and then 1.0 mL was pipetted onto replicate 5 cm plates of media 4 and 5 above. Most of the activated charcoal in the rinse medium was retained with the settled proembryos. These were also cultured in the dark for six weeks at about 22° C.

| Embryos Produced | Genotype A | Genotype B |
| --- | --- | --- |
| Medium 4 | 0.0 | 1.0 |
| Medium 5 | 11.8 | 35.8 |

These embryos also had the improved morphology noted for those produced by the first method.

Third Method—Activated Charcoal Medium then ABA Medium 1.0 mL of settled late stage proembryos was pipetted directly onto replicate 5 cm plates of medium 6 (activated charcoal only). These were cultured for one week at 22° C. in the dark then were transferred to medium 7 (ABA only) for five weeks. No cotyledonary embryos were produced for either genotype.

Fourth Method—ABA Medium With and Without Transfers 1.0 mL of settled late stage proembryos was pipetted directly onto replicate 5 cm plates of medium 7 (ABA only). These were cultured in the dark at about 22° C. One subset was maintained on the original medium for the entire six week period. The other subset was transferred to fresh medium of the same composition at the end of the second and fourth weeks, then maintained on the last medium until the end of the test.

| Embryos Produced | Genotype A | Genotype B |
| --- | --- | --- |
| Not transferred | 0.0 | 0.0 |
| Transferred | 2.0 | 3.3 |

The few cotyledonary embryos that developed were of poorer quality than those developed using the first and second methods. They did not show the prominent apical domes and had a shorter, often bulging, shape.

It is very evident that the combination of ABA and activated charcoal in the Embryo Development Medium is highly advantages from the standpoint of both numbers and quality of embryos produced. It appears that the charcoal is most effective when it is uniformly dispersed throughout the medium. However, it is also advantageous when it is localized around the growing embryos. It is believed that the charcoal could also be localized on the upper surface of the medium with similar good results. For example the activated charcoal could be on a filter paper or other type porous membrane which might also be used as a support surface for the growing embryos. It should be noted here that none of the media compositions used are represented as being optimized for any of the genotypes employed.

To the present time, using the procedures just outlined, about 3800 plantlets of *Picea abies* have been produced from 20 different genotypes of the species, and established in soil.

The use of the combined ABA-activated charcoal systems gave an additional entirely unexpected advantage. Somatic embryos generated on these media could be stored for extended periods of time at 4°-5° C. while remaining on the Embryo Development Medium. A number of genotypes of both *Pinus taeda* and *Picea abies* have now been stored for over three months without any evident deterioration or loss of vigor. Embryos of *Pseudotsuga menziesii* have been stored only for shorter periods at the present time but they too seem to have retained full vigor. These stored embryos develop normally into plantlets when moved to a rooting medium. Storage temperatures from just above the freezing point of the embryos (approximately 0° C.) to about 10° C. appear to be very satisfactory. It would appear that the temperature needs to be lowered only sufficiently to essentially inhibit metabolic action within the embryos. Storage is preferably done in the dark or on low light conditions. Prior to the present time long term storage usually required desiccation (e.g., see Buchheim, Colburn and Ranch 1989) or alginate gel encapsulation (e.g., Gupta and Durzan 1987).

It should be recognized that there is not one single set of culturing conditions that will be suitable for achieving somatic embryogenesis of all species or for all genotypes within a species. Tissue culture as a whole is a highly unpredictable science. This statement has even greater applicability to somatic embryogenesis. Adjustments in the mineral and plant hormone constituents of the culture media must frequently be made depending on the particular species and genotype being cultured. This applies to each of the various stages of culturing from explants to plantlets. These adjustments are considered to be within the routine experimental capability of those skilled in the art of tissue culture. The important discovery of the present invention is the use of a combination of abscisic acid and an adsorbent such as activated charcoal during the growth of late stage proembryos to cotyledonary embryos. This has given results that are far superior in terms of success and consistency than any process reported heretofore. The process has been successfully applied to all of the several species and many genotypes of coniferous plants studied to date and appears to be of general use for all coniferous species.

It will be understood that many variations can be made in the procedures described for the various culturing stages while still retaining within the spirit of the present invention. It is the intention of the inventors that such variations should be included within the scope of their invention if found defined within the following claims.

BIBLIOGRAPHY

Abo El-Nil, Mostafa. 1980: Embryogenesis of gymnosperm forest trees. U.S. Pat. No. 4,217,730.

Becwar, M. R., T. L. Noland, and S. R. Wann. 1987: A method for quantification of the level of somatic embryogenesis among Norway spruce callus lines. *Plant Cell Reports* 6:35–38.

Becwar, M. R., S. R. Wann, and R. Nagmani. 1988: A survey of initiation frequency of embryogenic callus among ten families of *Pinus taeda* (loblolly pine). *Abstracts*, 4th International Conifer Tissue Culture Work Group, Aug. 8–12, 1988, Saskatoon, Saskatchewan, Canada.

Boulay, M. P., P. K. Gupta, P. Krogstrup, and D. J. Durzan. 1988: Development of somatic embryos from cell suspension cultures of Norway spruce (*Picea abies* Karst.). *Plant Cell Reports* 7:134–137.

Bourgkard, F. and J. M. Favre. 1988: Somatic embryos from callus of *Sequoia sempervirens*. *Plant Cell Reports* 7:445–448.

Buchheim, Julie A., Susan M. Colburn, and Jerome P. Ranch. 1989: Maturation of soybean somatic embryos and the transition to plantlet growth. *Plant Physiology* 89:768–775.

Durzan, D. J. and P. K. Gupta. 1987: Somatic embryogenesis and polyembryogenesis in Douglas-fir cell suspension cultures. *Plant Science* 52:229–235.

Gupta, Promod K. and Don J. Durzan.
  1985: Shoot multiplication from mature trees of Douglas-fir (*Pseudotsuga menziesii*) and sugar pine (*Pinus lambertiana*). *Plant Cell Reports* 4:177–179.
  1986a: Somatic polyembryogenesis from callus of mature sugar pine embryos. *Bio/Technology* 4:643–645.
  1986b: Plantlet regeneration via somatic embryogenesis from subcultured callus of mature embryos of *Picea abies* (Norway spruce). *In Vitro Cellular and Developmental Biology* 22:685–688.
  1987: Biotechnology of somatic polyembryogenesis and plantlet regeneration in loblolly pine. *Bio/Technology* 5:147–151.

Hakman, Inger and Sara von Arnold. 1985: Plantlet regeneration through somatic embryogenesis in *Picea abies* (Norway spruce). *Journal of Plant Physiology* 121:149–158.

Hakman, Inger, Larry C. Fowke, Sara von Arnold, and Tage Eriksson. 1985: The development of somatic embryos in tissue cultures initiated from immature embryos of *Picea abies* (Norway spruce). *Plant Science* 38:33–35.

Johansson, Lars. 1983: Effects of activated charcoal in anther cultures. *Physiologia Plantarum* 59:397–403.

Johansson, Lars, Barbro Andersson, and Tage Eriksson. 1982: Improvement of anther culture technique: activated charcoal bound in agar medium in combination with liquid medium and elevated $CO_2$ concentration. *Physiologia Plantarum* 54:24–30.

Murashige, T. and F. Skoog. 1962: A revised medium for rapid growth and bioassays with tobacco tissue cultures. *Physiologia Plantarum* 15:473–493.

Nagmani, R. and J. M. Bonga. 1985: Embryogenesis in subcultured callus of *Larix decidua*. *Canadian Journal of Forest Research* 15:1088–1091.

Nagmani, R. and M. R. Becwar. 1988: Factors affecting somatic embryo development in loblolly pine. *Abstracts*, 4th International Conifer Tissue Culture Work Group, Aug. 8–12, 1988, Saskatoon Saskatchewan, Canada.

Singh, Hardev. 1978: "Embryo" in *Embryology of Gymnosperms*, Chapter 11, Gebruder Borntrager, Berlin.

Teasdale, Robert D., Pamela A. Dawson, and Harold W. Woolhouse. 1986: Mineral nutrient requirements of a loblolly pine. (*Pinus taeda* cell suspension culture. *Plant Physiology* 82:942–945.

Ziv, Meira and Geula Gadasi. 1986: Enhanced embryogenesis and plant regeneration from cucumber (*Cucumis sativus* L.) callus by activated charcoal in solid/liquid double-layer cultures. *Plant Science* 47:115–122.

We claim:

1. A method for reproducing coniferous plants by somatic embryogenesis which comprises:
    placing a suitable explant on an induction culture medium containing sufficient amounts of nutrients and plant growth hormones and growing a culture containing proembryos; and
    transferring the proembryos to a cotyledonary embryo development medium having exogenous abscisic acid in the range of about 5–100 mg/L and a sufficient amount of an adsorbent material to gradually reduce the concentration of abscisic acid over time, said culture being carried out for a sufficient time and under suitable environmental conditions to enable development of cotyledonary embryos, said combination of abscisic acid and adsorbent yielding greater quantities of cotyledonary embryos of greater vigor than media lacking the adsorbent material.

2. The method of claim 1 which further includes transferring the proembryos from the induction culture to an intermediate maintenance and multiplication culture medium having a significantly reduced level of plant growth hormones, prior to transferring the proembryos into the cotyledonary embryo development medium.

3. The method of claim 2 which further includes transferring the proembryos from the maintanance and multiplication medium into a late stage proembryo development culture medium having an osmotic potential in the range of 200–400 mM/kg, prior to transferring the proembryos into the cotyledonary embryo development medium.

4. The method of claim 1 in which the adsorbent material is selected from the group consisting of activated charcoal, silica gel, activated alumina, poly(vinylpyrrolidone), molecular sieves, and mixtures thereof.

5. The method of claim 4 in which the adsorbent material in the cotyledonary embryo development medium is activated charcoal.

6. The method of claim 5 in which the activated charcoal is present in a range of about 0.1–5.0 g/L of medium.

7. The method of claim 1 in which the adsorbent material is present in a range of about 0.25–2.5 g/L of culture medium.

8. The method of claim 1 in which the abscisic acid and adsorbent are uniformly dispersed throughout the medium.

9. The method of claim 1 in which the abscisic acid is uniformly present throughout the medium and the adsorbent material is present as a surface layer on a solid medium.

10. The method of claim 9 in which the adsorbent material is present on a supporting web.

11. The method of claim 1 in which the abscisic acid is uniformly present throughout the medium and the adsorbent material is present as a coating on the proembryos transferred to the medium.

12. The method of claim 1 in which the coniferous plant is *Picea abies*.

13. The method of claim 1 in which the coniferous plant is *Pinus taeda*.

14. The method of claim 1 in which the coniferous plant is *Pseudotsuga menziesii*.

15. The method of claim 1 in which the cotyledonary embryos are stored above their freezing point at a temperature in the range of 0°–10° C. under conditions of darkness or reduced light whereby they can be retained for extended periods of time without loss of vigor.

* * * * *